(12) United States Patent
Harrah et al.

(10) Patent No.: US 10,765,441 B2
(45) Date of Patent: Sep. 8, 2020

(54) DEVICES FOR MEDICAL PROCEDURES AND RELATED METHODS OF USE

(71) Applicant: Boston Scientific Scimed, Inc., Maple Grove, MN (US)

(72) Inventors: Timothy P. Harrah, Cambridge, MA (US); Christopher L. Oskin, Grafton, MA (US); Arpita Banerjee, Bangalore (IN); Sandesh Gavade, Bangalore (IN); Abhijit Takale, Pune (IN); Pavan Misra, Bangalore (IN); Michael Barenboym, Bedford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 709 days.

(21) Appl. No.: 15/416,858

(22) Filed: Jan. 26, 2017

(65) Prior Publication Data

US 2017/0215901 A1    Aug. 3, 2017

Related U.S. Application Data

(60) Provisional application No. 62/288,625, filed on Jan. 29, 2016.

(51) Int. Cl.
*A61B 17/00* (2006.01)
*A61B 17/221* (2006.01)
*A61B 1/00* (2006.01)

(52) U.S. Cl.
CPC ........ *A61B 17/221* (2013.01); *A61B 1/00133* (2013.01); *A61B 2017/003* (2013.01); *A61B 2017/0046* (2013.01); *A61B 2017/00367* (2013.01)

(58) Field of Classification Search
CPC ................ A61B 1/00133; A61B 1/018; A61B 2017/0046; A61B 2017/00469; A61B 1/00–1/32; A61B 17/22; A61B 2017/00296; A61B 2017/0034; A61B 2017/00367; A61M 25/0113; A61M 2025/09116

See application file for complete search history.

(56) References Cited

U.S. PATENT DOCUMENTS

| | | | |
|---|---|---|---|
| 4,616,648 A * | 10/1986 | Simpson | ............ A61M 25/0113 604/159 |
| 8,221,305 B2 * | 7/2012 | Suzuki | .................. A61B 1/018 600/104 |
| 2007/0299305 A1 * | 12/2007 | Murakami | ............. A61B 1/018 600/106 |

* cited by examiner

*Primary Examiner* — Sarah W Aleman
(74) *Attorney, Agent, or Firm* — Bookoff McAndrews, PLLC (57) ABSTRACT

A medical device may include a handle having an actuator, and a shaft coupled to the handle. The shaft may include a working channel. The medical device also may include a pair of friction rollers configured to be actuated by the actuator. The pair of friction rollers may be configured to receive an elongate member between one another, wherein actuation of the actuator may cause the pair of friction rollers to rotate and urge the elongate member to translate.

3 Claims, 5 Drawing Sheets

DEVICES FOR MEDICAL PROCEDURES AND RELATED METHODS OF USE

CROSS-REFERENCE TO RELATED APPLICATION(S)

This patent application claims the benefit under 35 U.S.C. § 119 to U.S. Provisional Patent Application No. 62/288,625, filed on Jan. 29, 2016, the entirety of which is incorporated herein by reference.

TECHNICAL FIELD

Various aspects of the present disclosure relate generally to medical devices. More specifically, the present disclosure includes medical devices with mechanisms for controlling the longitudinal movement of tools through endoscopic devices, and related methods of use.

BACKGROUND

Retrieval devices and systems allow physicians and other medical professionals to remove various materials from a patient, including organic material (e.g., blood clots, tissue, and biological concretions such as urinary, biliary, and pancreatic stones) and inorganic material (e.g., components of a medical device or other foreign matter). For example, concretions can develop in the kidneys, pancreas, ureter, or gallbladder, and cause blockages or other complications within the body. Minimally-invasive medical procedures may be used to remove these materials through a natural orifice, such as lithotripsy and ureteroscopy, or through an incision, such as percutaneous nephrolithotomy.

Current endoscopic systems have disadvantages, however. For example, ureteroscopic procedures typically require two or more people, wherein a physician controls the ureteroscope with both hands (one hand to grasp the handle and the other to hold the distal portion of the ureteroscope as it enters the urinary tract via the urethral meatus), and an assistant inserts a tool such as a basket, forceps, or a laser through a working channel of the ureteroscope and manipulates the tool. To remove a kidney stone, for example, a ureteroscope is used to gain access to the kidney, and a separate basket device is inserted into the working channel of the ureteroscope to remove or reposition the stone. In order to fragment larger stones into smaller pieces for removal, the basket device can be withdrawn from the working channel and substituted for a laser. After fragmenting the stone, the laser can be removed from the working channel and the basket device reinserted to capture the fragments.

This technique requires careful coordination. If communication between the physician and assistant is unclear, the assistant may require multiple attempts to successfully fragment and retrieve a stone or other material from the patient. Multiple attempts can increase risk to the patient, increase procedure time, and lead to tool damage for repeated unsuccessful attempts. Further, coordination between multiple people to control separate instruments simultaneously in a limited space can be logistically difficult and inconvenient, requiring awkward gripping and imprecise manipulation of the instruments.

SUMMARY

In one aspect, the present disclosure is directed to a medical device that may include a handle having an actuator, and a shaft coupled to the handle. The shaft may include a working channel. The medical device also may include a pair of friction rollers configured to be actuated by the actuator. The pair of friction rollers may be configured to receive an elongate member between one another, wherein actuation of the actuator may cause the pair of friction rollers to rotate and urge the elongate member to translate.

Actuation of the actuator may cause a first friction roller of the pair of friction rollers to rotate in an opposite direction from a second friction roller of the pair of friction rollers. Rotation of the actuator in a first direction may cause the elongate member to move distally. Rotation of actuator in a second direction that is opposite of the first direction may cause the elongate member to move proximally. The medical device may include a translation system coupling the actuator to the pair of friction rollers, wherein the translation system may be configured to configured to use a rotational force applied to the actuator to cause the pair of friction rollers to rotate. The translation system may include an endless belt coupled to both the actuator and to the pair of friction rollers. The endless belt may be tensioned such that the relative position of elongate member and the pair of friction rollers is fixed when no force is applied to the actuator. The actuator may be a rotatable thumbwheel, wherein the outer surface of the handle may include a thumbwheel surface at a proximal end of the handle, and wherein the thumbwheel may extend through the thumbwheel surface. The medical device may further include a gripping portion extending distally from the thumbwheel surface, and an access surface extending distally and radially outward from the gripping portion, wherein the access surface includes a port coupled to the first working channel. The medical device may further include a translation housing coupled to the access surface, wherein the pair of friction rollers may be disposed in the translation housing. The medical device may further include a mounting surface offset from and extending distally from the access surface, the mounting surface including one or more mating features configured to receive a tool handle assembly. The medical device may further include a translation housing coupled to the gripping portion, wherein the pair of friction rollers may be disposed in the translation housing. The translation housing may further include a mating flange, and wherein the gripping portion may include a mating feature configured to receive the mating flange. The pair of friction rollers may be biased toward one another. Each of the pair of friction rollers may include a rubber material disposed around its respective circumference, wherein the rubber material of a first friction roller of the pair of friction rollers may contact the rubber material of a second friction roller of the pair of friction rollers.

In yet another aspect, the present disclosure is directed to a medical device that may include a handle having a thumbwheel that extends through an outer surface of the handle, and a shaft coupled to the handle, the shaft including a working channel. The medical device also may include a sheath disposed through the working channel, and a tool disposed through the sheath and movable relative to the sheath. The medical device also may include a tool handle assembly mounted to the handle, the tool handle assembly having an actuator configured to move the tool relative to the sheath, and a pair of friction rollers configured to be actuated by the thumbwheel, wherein the pair of friction rollers may receive the sheath between one another, and wherein rotation of the thumbwheel may cause the pair of friction rollers to rotate and urge the sheath and the tool to move through the working channel.

The tool may be an expandable basket. Rotation of the thumbwheel in a first direction may cause the sheath and the tool to move distally together, and wherein rotation of actuator in a second direction that is opposite of the first direction may cause the sheath and the tool to move proximally together.

In yet another aspect, the present disclosure is directed to a method of performing a medical procedure. The method may include positioning an elongate member through a working channel of an endoscopic device, and positioning the elongate member adjacent at least one friction roller. The method also may include rotating a thumbwheel to cause the at least one friction roller to rotate and urge the elongate member through the working channel.

The thumbwheel and the at least one friction roller may be disposed within a translation device, wherein the method may further include securing the translation device to a rigid shaft of the endoscopic device.

BRIEF DESCRIPTION OF THE FIGURES

The accompanying drawings, which are incorporated in and constitute a part of this specification, illustrate various examples and together with the description, serve to explain the principles of the disclosure.

DETAILED DESCRIPTION

Examples of the present disclosure include medical devices useful in diagnostic and/or treatment procedures, such as breaking apart and retrieving autogenous materials and/or foreign materials from a patient. Medical devices according to the present disclosure may provide for a single operator to have longitudinal and/or rotational control of tools used in the diagnostic and/or treatment procedures.

An exemplary medical device 100 according to some aspects of the present disclosure is shown in FIGS. 1-4, comprising a handle 102 coupled to a shaft 104. The medical device 100 may be suitable for use in ureteroscopy, for example, but may be configured for use in other procedures and for diagnosis/treatment of other areas of a patient's body. The handle 102 may have any shape suitable for gripping and controlling the medical device 100, and may extend from a proximal end 101 toward a distal end 103. For example, the handle 102 may have an ergonomic shape designed to be held comfortably in the hand, e.g., the palm of the hand. The shaft 104 may extend from a proximal end 106 to a distal end 108, such that the proximal end 106 of the shaft may be coupled to (e.g., detachably or permanently connected to) the distal end 103 of the handle 102. The handle 102 and/or the shaft 104 may be disposable.

Figure 2:
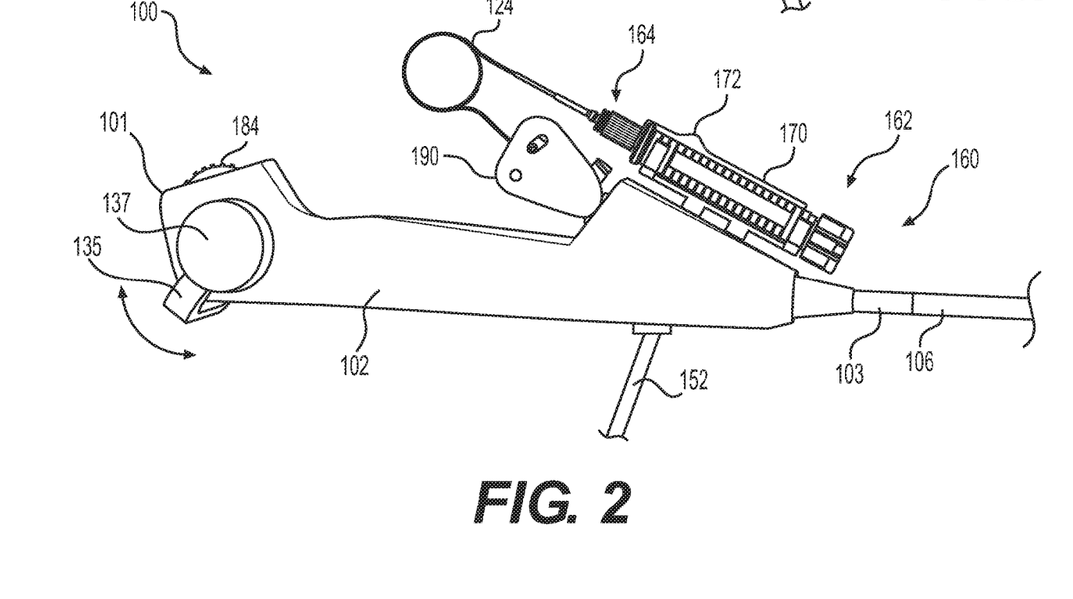
FIG. 2 is another side view of the medical device of FIG. 1.

The medical device 100 may include a steering mechanism for deflecting the shaft 104 along one or more planes. For example, the handle 102 may include an actuator 135 coupled to one or more portions of the shaft 104 at or near the distal end 108 of the shaft 104 via one or more control members, such as steering wires (not shown). Any suitable steering mechanism and/or actuators may be used. The actuator 135 may be pivotably coupled to the handle 102 via a post 137, as shown in FIG. 2, such that pivoting the actuator 135 about the post 137 moves the distal end 108 of the shaft 104 along a plane (e.g., left/right or up/down). That is, pivoting actuator 135 about post 137 may deflect the distal end 108 of the shaft 104 away from or toward a longitudinal axis 138 of the medical device 100. According to some aspects, the actuator 135 may include a locking device, such that the actuator 135 may be locked in place when the distal end 108 of the shaft 104 is in a desired position.

Figure 3:
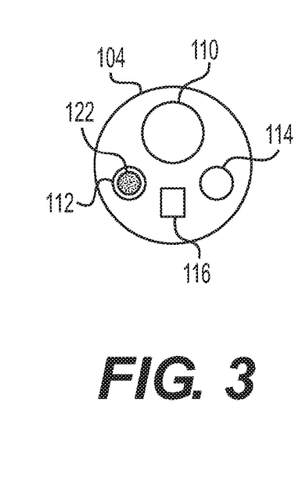
FIG. 3 is a distal end view of the medical device of FIG. 1

The shaft 104 may include at least one working channel, for example three working channels 110, 112, 114 as shown in cross-section in FIG. 3. According to some aspects, the medical device 100 may include two working channels (e.g., only working channels 110 and 112, or 110 and 114), or may include more than three working channels. Further, the working channels may have different shapes and/or sizes. For example, working channel 110 of FIG. 3 as shown is relatively larger than the other two working channels 112, 114, e.g., such that working channel 110 may serve as a main working channel 110. In some examples, the shaft 104 may include one or more electronic components 116, such as a camera or other imaging device, a light source, and/or other sensor. For example, the shaft 104 may include a camera lens ranging from about 0.5 mm$^2$ to about 2 mm$^2$ in size, or from about 0.75 mm$^2$ to about 1.5 mm$^2$ in size, e.g., approximately 1 mm$^2$ in size. Additionally or alternatively, one of the working channels 110, 112, 114, may provide a lumen for light delivery. For examples comprising a steering mechanism, the shaft 104 may include control channels (not shown) to house the steering control members.

In some aspects of the present disclosure, the handle 102 may include at least one port 150 (e.g., a luer port) in communication with one or more of the working channels 110, 112, 114, e.g., to allow for the insertion of tools (e.g., forceps, scissors, a grasper, a snare, a probe, a guidewire, a laser, an optical device, an imaging device), for irrigation, and/or for suction. For example, irrigation may be pumped through one or more of the working channels, e.g., working channel 110 and/or working channel 112, via the port 150 to provide lubrication and/or aid in visualization. The handle 102 may include an electronics hub or connector 152 for electrical connections, such as transferring data and/or powering a light source.

Further referring to FIG. 3, at least one of the working channels (or according to some aspects of the present disclosure, the only working channel), e.g., channel 112, may house a tool 122 configured to translate proximally and distally, such that the tool 122 may exit the distal end 108 of the shaft 104 for performing a procedure. Tool 122 may extend through a sheath 124. Tool 122 and sheath 124 may be configured to move together through channel 112 in some instances, and in other instances, may be moved relative to one another. For example, tool 122 and sheath 124 may be moved together during insertion into and removal from channel 112. Tool 122 and sheath 124 also may be moved together when an operator desires to adjust the longitudinal position of tool 122 when deployed inside the body. Tool 122 and sheath 124 may be moved relative to one another by when an operator desires to deploy tool 122, and also when an operator desires to collect the tool 122 after it is used.

Handle 102 may include a thumbwheel surface 154 at proximal end 101. The thumbwheel surface 154 may extend radially outward from the longitudinal axis 138 in the distal direction. Handle 102 may include a gripping portion 156 that extends from thumbwheel surface 154. Gripping portion 156 may extend distally from thumbwheel surface 154 and may include a plurality of surfaces arranged to create an ergonomic grip for the operator. An access surface 158 may extend distally and radially outward from the distalmost surface of gripping portion 156, and a mounting surface 159 may extend distally from access surface 158. Access surface 158 may be offset from longitudinal axis 138 of medical device 100, and mounting surface 159 may be offset from both access surface 158 and longitudinal axis 138.

Figure 1:
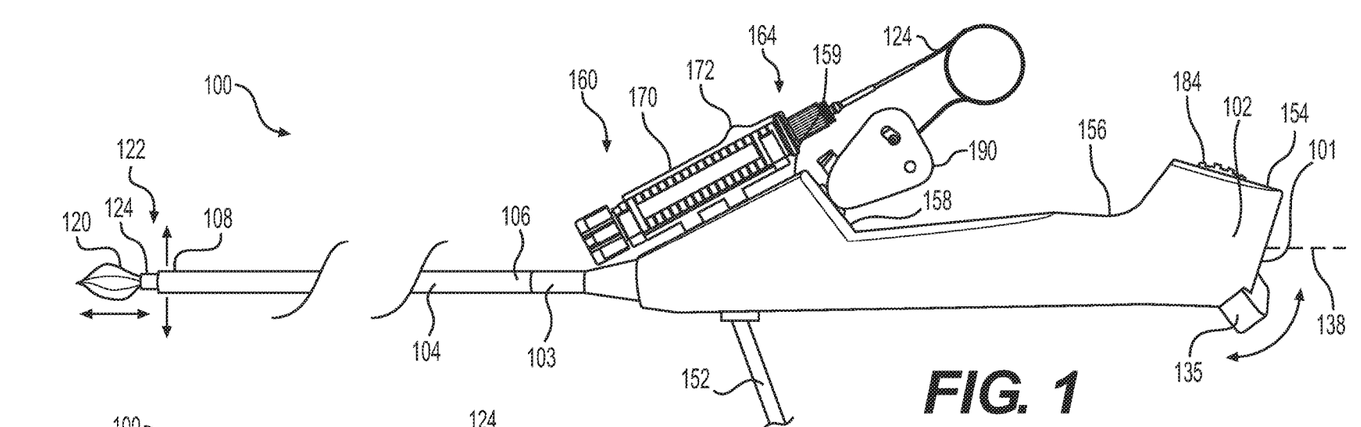
FIG. 1 is a side view of a medical device according to an example of the present disclosure.
Figure 4:
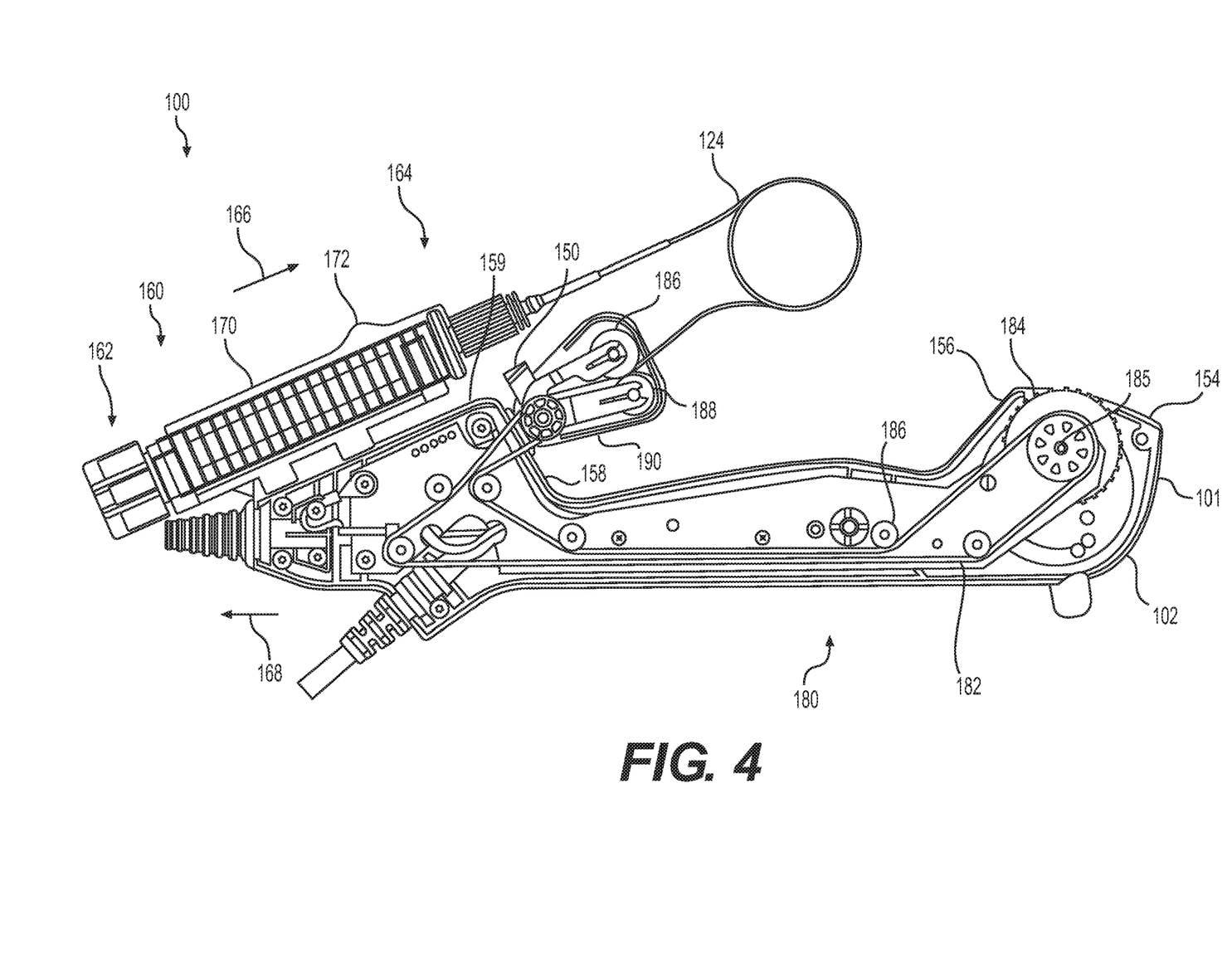
FIG. 4 is a side view of the medical device of FIG. 1, with portion of the medical device cutaway.

FIGS. 1, 2, and 4 illustrate a tool handle assembly 160 mounted to the mounting surface 159 of medical device 100. Tool handle assembly 160 may extend from a proximal end 162 toward a distal end 164. Tool handle assembly 160 may be oriented in a generally inverse configuration with respect to handle 102 such that tool handle assembly 160 extends distally along a first direction 166, while handle 102 extends distally in a second direction 168 that generally opposes the first direction 166. Tool handle assembly 160 may include an actuator 170 such as, e.g., a sliding mechanism, rotating mechanism, pushing mechanism, or the like. In the examples shown in FIGS. 1, 2, and 4, actuator 170 may include a protrusion 172 on its upper surface, on which the user may exert forces on actuator 170 using his or her thumb. Actuator 170 may be coupled to sheath 124 and include internal stops for limiting movement of the sheath 124 relative to the tool 122. A drive member (not shown) may be fixed to proximal end 162 of the tool handle assembly 160. It is understood that the tool handle assembly 160 may be formed in any conventional manner to control the movement of tool 122 relative to the sheath 124.

Tool handle assembly 160 may be mounted in other suitable locations and/or in other orientations with respect to handle 102. In the example shown in FIGS. 1, 2, and 4, tool handle assembly 160 is mounted on mounting surface 159 such that, when mounted, tool handle assembly 160 does not affect an operator's ability to access and grasp handle 102 via ergonomic gripping portion 156.

In some aspects of the present disclosure, the tool 122 may comprise an end effector 120, such as a basket as shown in FIG. 1. For example, the tool 122 may be a basket device configured to capture stones and other materials. Any other suitable tools may be used according to the present disclosure, including, but not limited to, forceps, scissors, a grasper, a snare, a probe, and/or other tools. Tools may comprise materials such as metals, metal alloys, shape memory materials, polymers (including plastics and thermopolymers), or any combinations thereof. Tool 122 may also be a laser fiber. The proximal end of the laser fiber may be connected to an energy source, such as a Holmium laser, for example. When the laser is activated, optical (laser) energy may travel from the proximal end of the fiber to a distal end of the fiber and into the body to treat, e.g., a kidney stone.

The basket (or other expandable end effector) may be configured to self-expand, e.g., having a compressed configuration within the sheath 124 (or a laser fiber or basket device) and an expanded configuration outside the sheath 124, such that, in the expanded configuration past the distal end 108 of the shaft 104 and once deployed outside of sheath 124, the basket may be used to retrieve materials and objects captured within the basket. For example, the inner surface of the sheath 124 may serve to compress the basket. In some cases this may help to minimize the size of the medical device 100. For example, according to some aspects, the basket may have a cross-sectional diameter ranging from about 0.5 Fr (0.17 mm) to about 1.5 Fr (0.5 mm), e.g., about 1 Fr (0.33 mm), and the working channel 112 may have a cross-sectional diameter ranging from about 1 Fr (0.33 mm) to about 2 Fr (0.67 mm), e.g., about 1.5 Fr (0.5 mm).

In some aspects, the basket may include a wire, e.g., a wire filament that splits into three, four, or more wires in a generally bulbous shape that converge at the tip. Additionally or alternatively, the basket may comprise a mesh or net-like portion towards the proximal end of the basket, e.g., to capture relatively smaller pieces of materials, such as pulverized stone. Further, for example, the basket may be configured as a net, e.g., comprising a mesh, to facilitate the retrieval of small fragments of material. A guidewire and/or laser may be inserted into one of the working channels, e.g., working channel 110 or 114, during a procedure. For example, a laser may be used to break apart relatively larger pieces of materials within the body to facilitate removal of the material with the basket.

The basket may include Nitinol or other suitable flexible materials. For example, the basket may include Nitinol such that the basket is self-expandable. Alternatively, the basket may be configured to expand manually once extended beyond the distal end of the sheath 124, e.g., via a suitable control mechanism in the tool handle assembly 160.

Sheath 124 containing tool 122 may extend distally from the distal end 164 of tool handle assembly 160, through working channel 112, and out of the distal end 108 of shaft 104. The longitudinal translation of sheath 124 may be controlled by medical device 100 via a translation system 180. Translation system 180 may be a belt and pulley system comprising an endless belt 182 driven by a thumbwheel 184 that rotates about a point 185 disposed within proximal end 101 of handle 102. The thumbwheel 184 may be configured as a driving wheel of the belt and pulley translation system 180, which, through one or more intermediate rollers 186 and/or gears (not shown in the examples of FIGS. 1-4), is configured to control, urge, or cause, the longitudinal movement of sheath 124 via a pair of friction rollers 186 and 188. Any suitable number of rollers and/or gears may be utilized in any configuration in order to convert a rotational force applied to thumbwheel 184 into the longitudinal movement of tool 122 and sheath 124.

Friction rollers 186 and 188 may be disposed in a translation housing 190, and may be positioned adjacent one another such that a very small distance is disposed between friction rollers 186 and 188. It is also contemplated that there may be no distance between friction rollers 186 and 188. Friction rollers 186 and 188 may include a high-friction material, e.g., rubber, along their respective circumferences. The rubber material of friction roller 186 may contact the rubber material of friction roller 188. Friction rollers 186 and 188 may be biased toward one another by, e.g., an elastic biasing member. Sheath 124 may be positioned between friction rollers 186 and 188 such that the rotation of rollers 186 and 188 moves sheath 124 in a longitudinal direction. The high-friction material may promote the longitudinal movement of sheath 124 positioned between the friction rollers 186 and 188. Translation system 180 may be configured that when thumbwheel 184 is rotated in a first direction (e.g., clockwise), rollers 186 and 188 may rotate and cause sheath 124 to move distally relative to shaft 104. Thumbwheel 184 may be rotated in a second direction that is opposite of the first direction (e.g., counterclockwise) to urge or cause rollers 186 and 188 to move proximally relative to shaft 104.

Rollers 186 and 188 may rotate simultaneously in opposite directions to effect longitudinal movement of sheath 124. For example, in the example shown in FIG. 4, roller 186 may rotate in a clockwise direction while roller 188 rotates in a counterclockwise direction in order to move sheath 124 distally relative to shaft 104. In the same example of FIG. 4, roller 186 may rotate in a counterclockwise direction while roller 188 rotates in a clockwise direction in order to move sheath 124 proximally relative to shaft 104. Other suitable arrangements are also contemplated based upon the relative positioning of translation housing 190 and handle 102. For example, roller 186 may rotate in a clockwise direction while roller 188 rotates in a counterclockwise direction in order to move sheath 124 proximally, as opposed to distally, relative to a different shaft and vice versa.

Belt 182 of translation system 180 may be sufficiently tensioned in order to maintain and lock the position of tool 122 when no force is applied to thumbwheel 184. This may help maintain the position of tool 122 within the body without requiring active input from the operator. That is, once the tool 122 is placed in a desired position, the operator may utilize his or her hand which was manipulating thumbwheel 184 to manipulate other devices.

In some examples, thumbwheel 184 may be replaced by a gear driven by a motor. The motor may be actuated by a switch or other mechanism which may be disposed on the outer surface of handle 102, for example, on thumbwheel surface 154. In one example, the switch may be a sliding switch with intuitive and/or tactile feedback. For example, the switch may be configured such that when it is pushed in the distal direction, tool 122 and sheath 124 may be moved distally. When the switch is pulled proximally, tool 122 and sheath 124 may be pulled proximally. The switch may be pressure-sensitive, and may control the output of the motor based on the amount of pressure applied to the switch by the operator. Thus, the tool 122 and sheath 124 may be moved at a faster rate when more pressure is applied to the switch.

Figure 5:
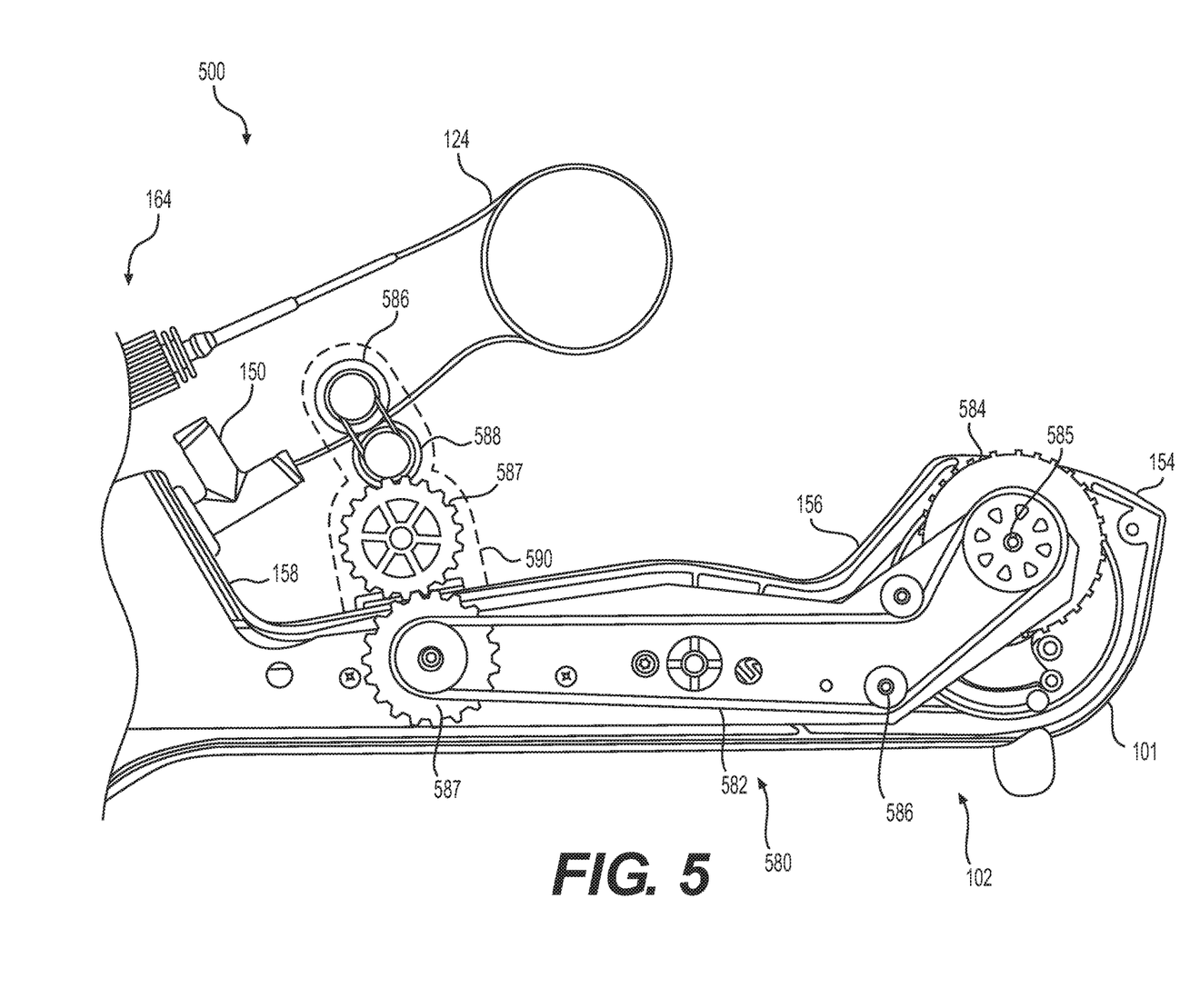
FIG. 5 is a side view of a medical device according to another example of the present disclosure, with a portion of the medical device cutaway.
Figure 6:
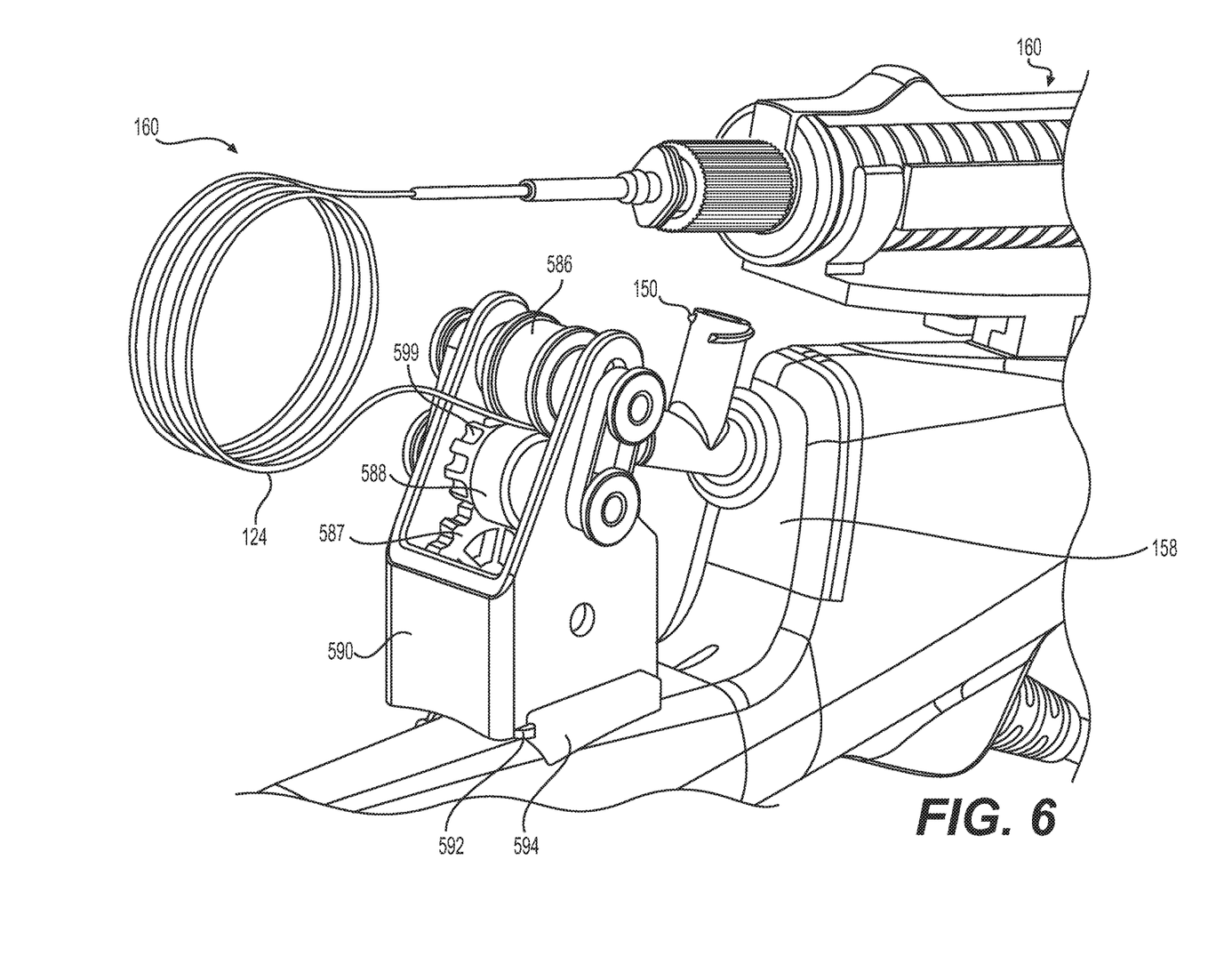
FIG. 6 is a perspective view of the medical device of FIG. 5.

FIGS. 5 and 6 depict a medical device 500 that is substantially similar to medical device 100 described above, except that medical device 500 may include a translation system 580 instead of translation system 180. Translation system 580 may be a belt and pulley system comprising an endless belt 582 driven by a thumbwheel 584 that rotates about a point 585 disposed within proximal end 101 of handle 102. The thumbwheel 584 may be configured as a driving wheel of the belt and pulley translation system 580, which, through one or more intermediate rollers 586 and/or gears 587, is configured to control the longitudinal movement of sheath 124 via a pair of friction rollers 586 and 588. Friction rollers 586 and 588 may operate in a substantially similar manner as rollers 186 and 188 described above in order to move sheath 124 longitudinally. Friction rollers 586 and 588 may be driven directly by a gear 599 that is coupled to one of rollers 586 and 588 instead of being driven directly by belt 582. In one example, gear 599 may be coaxial with one of rollers 586 and 588. Friction rollers 586 and 588 may be disposed in a translation housing 590, which may extend from gripping portion 156 of handle 102. Translation housing 590 may include one or more mating flanges 592 that may be received by corresponding mating features 594 that extend from a surface of gripping portion 156. Mating flanges 592 and mating features 594 may form a tongue and groove joint. Translation housing 590 also may be configured to mount to a surface of handle 102 in any other suitable manner.

Figures 7, 8:
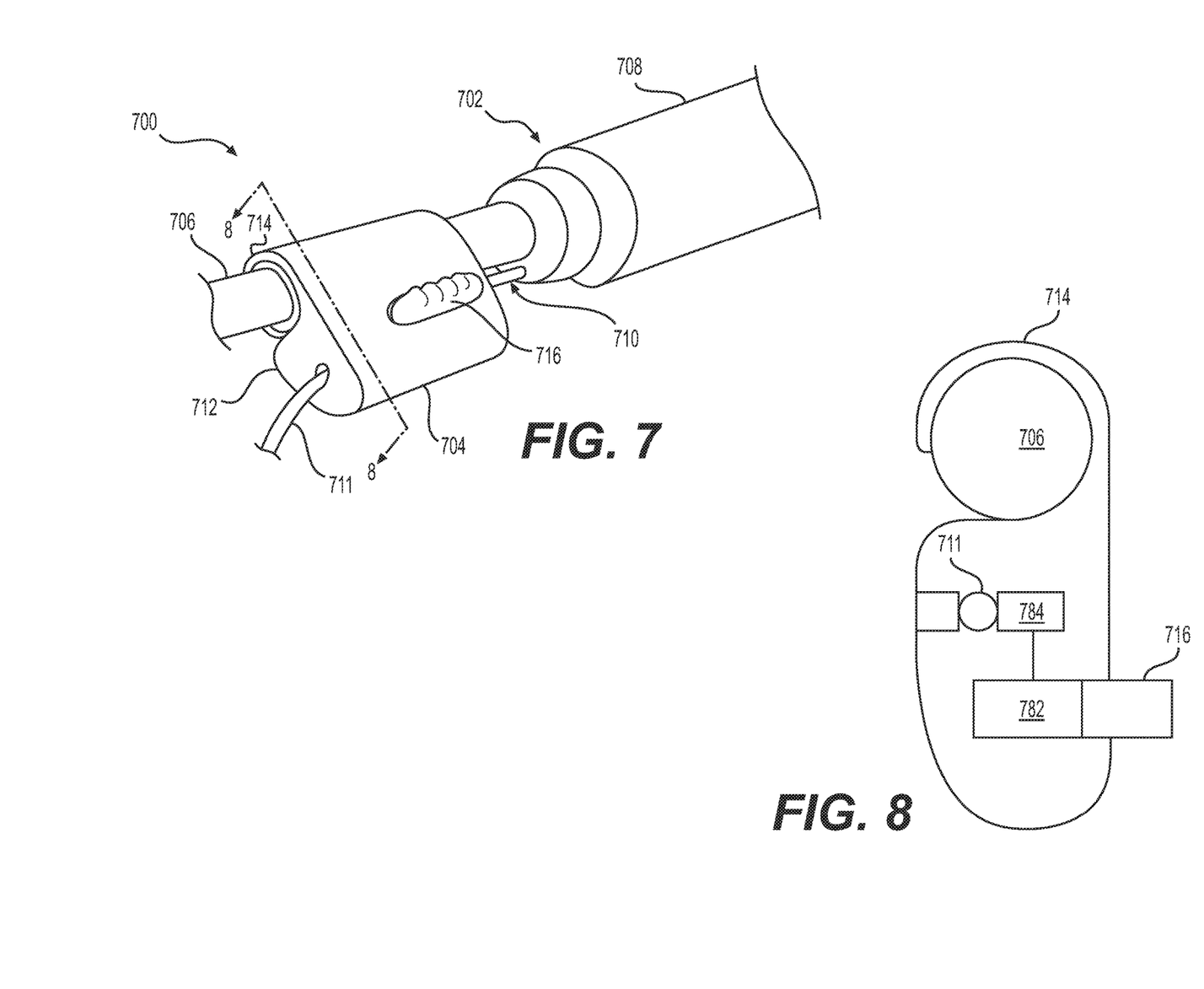
FIG. 7 is a perspective view of a medical device according to another example of the present disclosure.
FIG. 8 is an end view of a portion of the medical device of FIG. 7.

A medical device 700 is shown in FIGS. 7 and 8. Medical device 700 may include an endoscopic device 702 coupled to a translation device 704. Endoscopic device 702 may include a shaft 706 (e.g., a rigid or semi-rigid shaft), and an elongate member 708 that extends distally from the distal end of shaft 706. Elongate member 708 may be the portion of endoscopic device 702 that is configured to be inserted into a patient. Elongate member 708 may include an opening 710 at its proximal end that is configured to receive a fiber 711, e.g., a laser fiber 711. Opening 710 may receive other objects, such as, e.g., tool 122 and sheath 124.

Translation device 704 may include a housing 712 and a mating section 714 that extends from housing 712. Mating section 714 may be formed as a split tube that is configured to wrap around a shaft of an endoscopic member, such as, e.g., shaft 706. Mating section 714 may include a longitudinal opening 715 that extends along a substantial entirety of the length of mating section 714. The opening 715 may allow the split tube to be placed around the shaft 706. Once disposed around the shaft 706 of endoscopic member 702, mating section 714 may be secured to the shaft 706 in any suitable manner, such as, e.g., friction fits, clamps, or the like. Mating section 714 may be rigid such that mating section 714 is snapped onto shaft 706. In other examples, mating section 714 may be flexible and may be wrapped around the shaft 706.

Fiber 711 may extend through housing 712 via one or more apertures and lumens. The longitudinal translation of fiber 711 through endoscopic device 702 may be controlled by translation device 704 via a translation system 780. Translation system 780 may be any suitable system configured to convert a rotational force applied to a thumbwheel 716 to move fiber 711 longitudinally. In the example shown in FIGS. 7 and 8, thumbwheel 716 may be a gear that drives a gear 782. Gear 782 may be coupled to a friction roller 784. Friction roller 784 may engage fiber 711 and apply a tension to fiber 711 along with an interior surface 786 of housing 712. Fiber 711 may be positioned between friction roller 784 and surface 786 such that the rotation of roller 784 moves fiber 711 in a longitudinal direction. Translation system 780 may be configured such that when thumbwheel 716 is rotated in a first direction (e.g., clockwise), roller 784 may rotate and cause fiber 711 to move distally relative to shaft endoscopic device 702. Thumbwheel 716 may be rotated in a second direction that is opposite of the first direction (e.g., counterclockwise) to cause fiber 711 to move proximally relative to endoscopic device 702.

In some examples, a locking mechanism may fix the position of laser fiber 711 relative to a tip of endoscopic device 702 in a hands-free fashion. Thus, mating section 714 may be fixed to the shaft 706 with a slip fit using a suitably high friction material (like silicone) that would enable the device to remain stationary under nominal conditions. Thumbwheel 716 then may actuate a locking mechanism to fix the laser fiber position. As set forth above, this may be a friction-based mechanism. Alternatively, thumbwheel 716 may permit stability under nominal conditions and limit translation along shaft 706 to provide limited (e.g., fully manual) advancement of fiber 711 relative to the tip of endoscopic device 702.

Examples of the present disclosure may reduce the number of operators needed to complete various procedures by allowing a single operator to control a tool disposed through an endoscopic member. In the case of laser treatments, examples of the present disclosure may help prevent the laser from firing in the wrong direction when, for example, the user inadvertently moves thereby changing the firing position of the laser. This may help prevent damage to imaging devices by the laser.

Other examples of the present disclosure will be apparent to those skilled in the art from consideration of the specification and practice of the examples disclosed herein. While certain features of the present disclosure are discussed within the context of exemplary procedures, the devices, instruments, and methods are not so limited and may be used in other areas of the body, and for other medical procedures according to the general principles disclosed. It is intended that the specification and examples be considered as exemplary only, with a true scope and spirit of the present disclosure being indicated by the following claims.

We claim:

1. A medical device, comprising:
   a handle having a thumbwheel that extends through an outer surface of the handle and a gear that extends from a body of the handle and through the outer surface of the handle;
   a shaft coupled to the handle, the shaft including a working channel;
   a sheath disposed through the working channel;
   a tool disposed through the sheath and movable relative to the sheath;
   a tool handle assembly mounted to the handle, the tool handle assembly having an actuator configured to move the tool relative to the sheath; and
   a pair of friction rollers positioned entirely outside the body of the handle and operatively coupled to the gear, wherein the pair of friction rollers is configured to be actuated by the thumbwheel, wherein the pair of friction rollers receive the sheath between one another, and wherein rotation of the thumbwheel causes the gear to rotate, thereby causing the pair of friction rollers to rotate and urge the sheath and the tool to move through the working channel.

2. The medical device of claim 1, wherein rotation of the thumbwheel in a first direction causes the sheath and the tool to move distally together, and wherein rotation of actuator in a second direction that is opposite of the first direction causes the sheath and the tool to move proximally together.

3. The medical device of claim 1, further comprising a second gear operatively coupled to the pair of friction rollers, wherein the second gear operatively couples to the gear on the outer surface of the handle.

* * * * *